United States Patent
Simon et al.

(10) Patent No.: US 6,731,388 B1
(45) Date of Patent: May 4, 2004

(54) METHOD OF MEASURING SURFACE PLASMON RESONANCE USING INTERFERENCE STRUCTURE OF REFLECTED BEAM PROFILE

(75) Inventors: Henry J. Simon, Sylvania, OH (US); Robert T. Deck, Toledo, OH (US); Richard V. Andaloro, Toledo, OH (US)

(73) Assignee: The University of Toledo, Toledo, OH (US)

( * ) Notice: Subject to any disclaimer, the term of this patent is extended or adjusted under 35 U.S.C. 154(b) by 223 days.

(21) Appl. No.: 09/943,696

(22) Filed: Aug. 31, 2001

(51) Int. Cl.$^7$ ................................................ G01N 21/55
(52) U.S. Cl. ........................................................ 356/445
(58) Field of Search ........................................ 356/445

(56) References Cited

U.S. PATENT DOCUMENTS 4,889,427 A  * 12/1989  Van Veen et al. ............ 356/445
4,997,278 A  *  3/1991  Finlan et al. ................. 356/445
5,846,843 A    12/1998  Simon

OTHER PUBLICATIONS

"Theory of Prism–Film Coupler and Thin Film Light Guides"; P.K. Tien and R. Ulrich; Journal of the Optical Society of America, 60, 1325 (1970).

"Theory of the Prism–Film Coupler by Plane–Wave Analysis"; R. Ulrich; Journal of the Optical Society of America, 60, 1337–1350 (1970).

"Excitation of Surface Eletromagnetic Waves in Attenuated Total Reflection Prism Configurations"; W.P. Chen et al.; Phys. Rev. Letters 37, 993 (1976).

"Long–Range Surface Plasma Waves on Very Thin Metal Films"; D. Sarid; Physical Review Letters 47, 1927–1930 (1981).

"Surface Plasmon Resonance for Gas Detection and Bio-sensing"; Lieberg, Nylander and Lundstrom; Sensors and Actuators, vol. 4, 299 (1983).

"Atenuated total reflectance from a layered silver grating with coupled surface waves"; Zhan Chen and Henry Simon; Journal of the Optical Society B, vol. 5, 1396 (1988).

* cited by examiner

*Primary Examiner*—Richard A. Rosenberger
(74) *Attorney, Agent, or Firm*—MacMillan, Sobanski & Todd, LLC (57) ABSTRACT

Changes in optical properties of layered materials are measured by directing an incident wave of finite transverse dimensions toward layered materials under conditions that will produce a propagating surface mode or a waveguide mode in the layered materials. The intensity distribution is measured within the transverse beam profile of the total reflected beam. The profile shows asymmetric structure associated with the excitation of the propagating surface mode or a wave-guide mode. The index of refraction of the layered materials is modified and the reshaped intensity distribution within the transverse beam profile of the total reflected beam is again measured under the same incidence conditions. The measured intensity distributions are compared to detect differences in the indexes of refraction in the layered materials.

33 Claims, 4 Drawing Sheets

METHOD OF MEASURING SURFACE PLASMON RESONANCE USING INTERFERENCE STRUCTURE OF REFLECTED BEAM PROFILE

TECHNICAL FIELD

The present invention relates to a method of measuring changes in optical properties of layered materials, including using a sensor employing a propagating surface mode or waveguide mode in the layered materials for use in biological, biochemical and chemical testing. More particularly the present invention relates to an immunosensor for monitoring the physical interactions between two biologically relevant molecules.

BACKGROUND OF THE INVENTION

A surface plasmon resonance is the oscillation of free electrons that exists at a metal boundary induced by a time varying electric field. The phenomenon of surface plasmon resonance (SPR) can be used to detect minute changes in the refractive index of layers near a metal surface. The SPR is affected by the refractive index of the material adjacent to a metal surface and it is this dependence that forms the basis of the sensor mechanism.

In the case of immunosensors, as a reaction between an antigen and an antibody proceeds, the surface properties change from their original state. While antibodies are immobilized on the surface, the properties of the surface change when a solution containing a corresponding antigen is brought into contact with the surface. This interaction allows the antigen to bind with the antibody. The change in the optical properties of the surface can then be monitored with a suitable sensor.

Generally, SPR may be achieved by using the evanescent wave that is generated when a P-polarized light beam is totally internally reflected at the interface between two media, e.g. the interface between a liquid medium such as a blood serum, which has a positive dielectric constant, and a metallic medium, such as a metal film, which has a negative dielectric constant. The SPR is excited when the incident angle of the light beam is tuned to a particular angle of incidence at which the electrons in the metallic medium resonantly absorb the energy of the light beam. As a direct consequence the energy in the reflected light beam is strongly diminished. This process is referred to as attenuated total reflection (ATR).

SPR biosensors work on the principle of measuring the change in the ATR when the optical properties of the medium adjacent to the metal are changed. Specifically, antigens in a first solution are initially caused to be immobilized on the metal surface. The optical properties of the surface change when a second solution, sometimes referred to as the analyte medium, which contains a corresponding antibody, is brought into contact with the surface thus allowing the antigen to bind with the antibodies. The angular sensitivity of the ATR feature to adsorbed biological layers on the metal surface has made the SPR device a suitable sensor to monitor the binding reaction.

One particular form of SPR, commonly referred to as the Kretschmann mode, is more properly described as a single boundary mode since the surface wave achieves its peak value at only a single metal/dielectric interface. In practice a sensor system makes use of a light beam that is incident to the surface and reflected. Commonly this is a divergent beam from a light emitting diode (LED) followed by a lens system to produce a slightly focused incident beam with an angular spread of a few degrees. The reflected light beam is generally captured in an optical detector, such as in the form of a linear pixel array. The design of many sensor systems is based on the detection of the angular shift of the entire ATR pattern due to the antibody/antigen binding reaction. A paper published under the title, "Surface plasmon resonance for gas detection and biosensing", by Lieberg, Nylander and Lundstrom in Sensors and Actuators, Vol. 4 at page 299, further describes the SPR technique recited above, the entire paper is hereby incorporated herein by reference.

A more sensitive surface plasmon sensor is described in U.S. Pat. No. 5,846,843 to Simon, which discloses a long range SPR sensor, the disclosure of which is incorporated herein by reference. The sensor includes a first dielectric medium and a second dielectric medium having approximately matching indices of refraction. A thin metal film is located between the first and second dielectric media. A beam of electromagnetic radiation is introduced into the sensor layer assembly in a manner that causes the long-range surface plasmon resonance to occur. This resonance may be achieved through the formation of diffraction gratings at each of the metal/dielectric interfaces as described in U.S. Pat. No. 5,846,843. The long-range surface plasmon (LRSP) can also be termed a double boundary mode as the surface wave achieves its peak value at both metal/dielectric interfaces. The basic diffraction-coupled LRSP phenomenon is further described in a paper entitled, "Attenuated Total Reflectance From a Layered Silver Grating with Coupled Surface Waves", by Zhan Chen and H. J. Simon in the Journal of the Optical Society B 5, 1936 (1988), the entire paper is incorporated herein by reference.

The method of detecting the binding reaction between the antibody and antigen is identical for both the single boundary Kretschmann mode and the double boundary LRSP mode. In both cases the multilayer assembly is rotated around an axis perpendicular to the plane of incidence to produce a scan in the incident angle. There exists an optimum angle, sometimes referred to simply as the plasmon angle, at which the phenomenon of surface plasmons is observed by manifesting itself as a sharp attenuation of the total reflected (ATR) beam. This angle sensitively depends upon the index of refraction of the second dielectric medium, which is commonly a liquid serum. Thus, the binding reaction between the antibody and antigen changes the value of the plasmon angle. The angle of incidence of the beam is varied to detect the plasmon angle. In practice the plasmon angle is first measured by means of an ATR angle scan with a serum that does not contain the test antibody and then a second time after the antibody is added to the serum. From the shift in the two angular ATR scans the shift in plasmon angle is deduced. Therefore, measuring the shift in the angular position of the minimum in the reflectivity provides a quantitative-measure of the antibodies absorbed from the sample. A sensitive measurement of the antibodies absorbed is obtained because the measured ATR characteristics are strongly dependent upon the amount of antigens attached to the layer of antibodies. It should be noted that the primary physical quantity measured in this system as well as in most, if not all, current SPR sensors, is the total ATR beam intensity at each angle of incidence within a narrow angular interval, including the plasmon angle.

The theoretical basis for understanding the ATR phenomenon, associated with the resonant excitation of surface waves, is generally based on an infinite plane wave approximation for the incident light wave. While this method has been adequate to detect changes in surface properties, it would be beneficial to provide an improved method with greater sensitivity.

SUMMARY OF THE INVENTION

The above objectives as well as other objectives not specifically enumerated are achieved through the measurement of changes in optical properties of layered materials by first directing an incident wave toward layered materials under coupling conditions that will produce a propagating surface mode in the layered materials. Next, the intensity distribution within the transverse beam profile of the coupled output reflected beam is measured at a single value of the angle of incidence at or near the plasmon angle. Then, the index of refraction of the layered materials is modified and the intensity distribution within the transverse beam profile of the coupled output reflected beam is re-measured. Finally, the measured intensity distributions are compared to detect differences in the indices of refraction in the layered materials.

Another aspect of the present invention involves measuring changes in optical properties of layered materials by directing an incident wave toward layered materials under coupling conditions that will produce a propagating waveguide mode in the layered materials. Next, the intensity distribution within the transverse beam profile of the coupled output reflected beam is measured. Then, the index of refraction of the layered materials is modified and the intensity distribution within the transverse beam profile of the coupled output reflected beam is re-measured. Finally, the measured intensity distributions are compared to detect differences in the indices of refraction in the layered materials.

Various objects and advantages of this invention will become apparent to those skilled in the art from the following detailed description of the preferred embodiments, when read in light of the accompanying drawings.

DETAILED DESCRIPTION OF THE INVENTION

Figure 1:
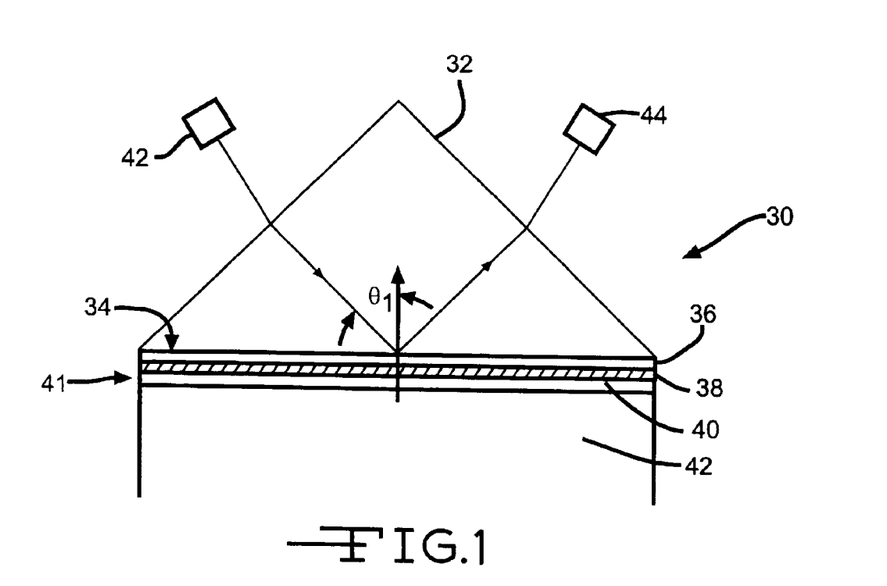
FIG. 1 is a sectional view of a biosensor that can be used with the method of the present invention to obtain a long-range surface plasmon resonance where the biosensor employs a prism coupler.

FIG. 1 is a sectional view and shows the optical layer structure of a sensor 30 employing a prism to obtain a long range surface plasmon. The sensor 30 includes a prism 32 where one prism face 34, preferably the hypotenuse, has a number of layers, i.e., layered materials, attached thereto. The prism 32 is made of glass or a plastic material having a refractive index larger than that of the layered dielectric media 36 and 40. The material should also be transparent to electromagnetic radiation. The first layer 36 is a dielectric medium. The second layer 38 is preferably a metal, and further preferred is the use of gold. The refractive index of the first dielectric medium 36 approximates the effective refractive index of the second dielectric medium 40. In a preferred embodiment, the refractive index of the first dielectric medium 36 is about 1.35 or that of an aqueous solution. Below the layers 36, 38 is an assay layer 40 that is, generally, a liquid containing a biological medium to be monitored. The index of refraction of the prism 32 is greater than the index of refraction of the biological assay 40. Another biological layer 42 can then brought into contact with the assay layer 40. This layer 42 contains molecules that can interact with the molecules in the assay layer 40. In a preferred embodiment, the assay layer 40 is blood having an index of refraction of about 1.35. The prism 32 preferably has an index of refraction of about 1.5.

These layers 36, 38, 40, form a structure 41 that is similar to the double-grating structure shown in FIG. 2 and as described below. This structure 41 also performs the function of combining the antibodies and antigens in a similar manner as with the double-grating structure, described below. A source of radiation 42 and an optical detector 44 are also included in the biosensor assembly. The source of radiation 42 preferably emits a well-collimated beam of light. The angle of incidence of the light is rotated to the angle $\theta_1$, the surface plasmon angle, at which a sharp attenuation in the strength of the total internally reflected beam is observed. The optical detector 44, which can be any suitable device for measuring light, such as a linear pixel array, generally captures the reflected light beam.

Figure 2:
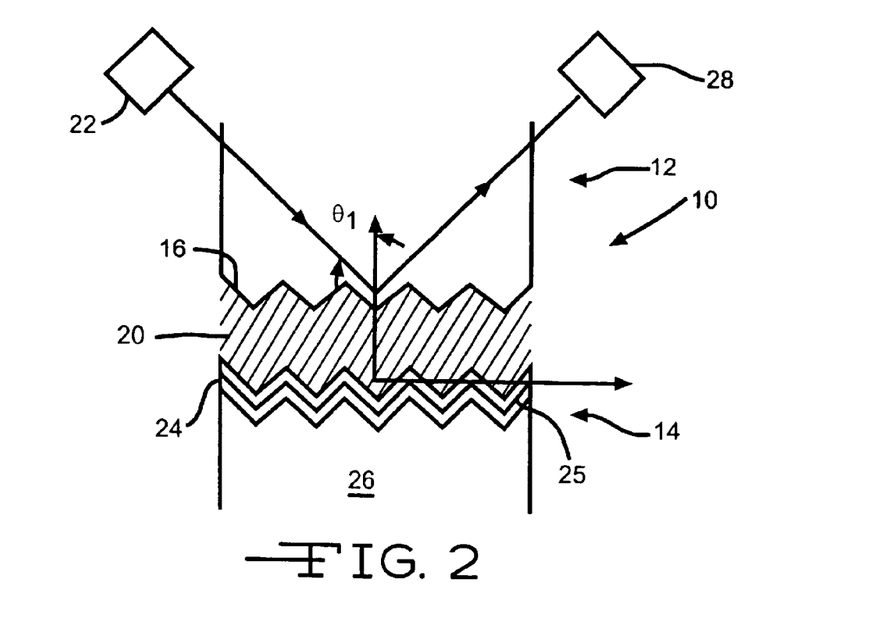
FIG. 2 is a sectional view of a second embodiment of a biosensor that can be used with the method of the invention to obtain a long-range surface plasmon resonance, where the biosensor employs a diffraction double-grating.

FIG. 2 is a sectional view and shows the optical layer structure of a sensor 10 employing a grating structure to obtain a long-range surface plasmon resonance. The sensor 10 includes a first dielectric medium 12 and a second dielectric medium 14. The first dielectric medium 12 is a material in which an electromagnetic wave can be propagated with a minimum dissipation of power. The first dielectric medium 12 is typically a refractive medium such as glass or plastic material and is transparent to electromagnetic radiation. More importantly, the refractive index of the first dielectric medium 12 is approximately the same as the effective refractive index of the second dielectric medium 14. In a preferred embodiment, the refractive index of the first dielectric medium 12 is about 1.35, or that of an aqueous solution. Formed at the bottom surface of the first dielectric medium 12 is a grating surface 16. The grating surface 16 may be an assembly of narrow grooves having inclined sidewalls. A preferred embodiment of the first dielectric medium 12 and the grating surface 16 would be in the form of a compact disc as is well known in the art.

Formed on the bottom grating surface 16 of the first dielectric material 12 is a thin metal film of uniform thickness. Consequently, both surfaces of the metal film replicate the contour of the grating surface 16 of the first dielectric medium 12 thereby producing a double-grating structure 20. Next, the sensor 10 has a first organic layer 24, a second organic layer 25 and a liquid solution 26. By means of a coupling technique such as is known in biotechnology, ligands in the first organic layer 24 are bound to the double-grating structure 20 and serve to interact with the specific molecules present in the liquid solution 26 thereby forming the second organic layer 25. A source of radiation 22 and an optical detector 28 complete the assembly. The source of radiation 22 preferably emits a well-collimated beam of light. The angle of incidence of the light is rotated to the angle $\theta_1$, the surface plasmon angle, at which a sharp attenuation in the strength of the total internally reflected beam is observed. An optical detector can be any type of light detector, such as a linear pixel array, and generally captures the reflected light beam.

Figure 3:
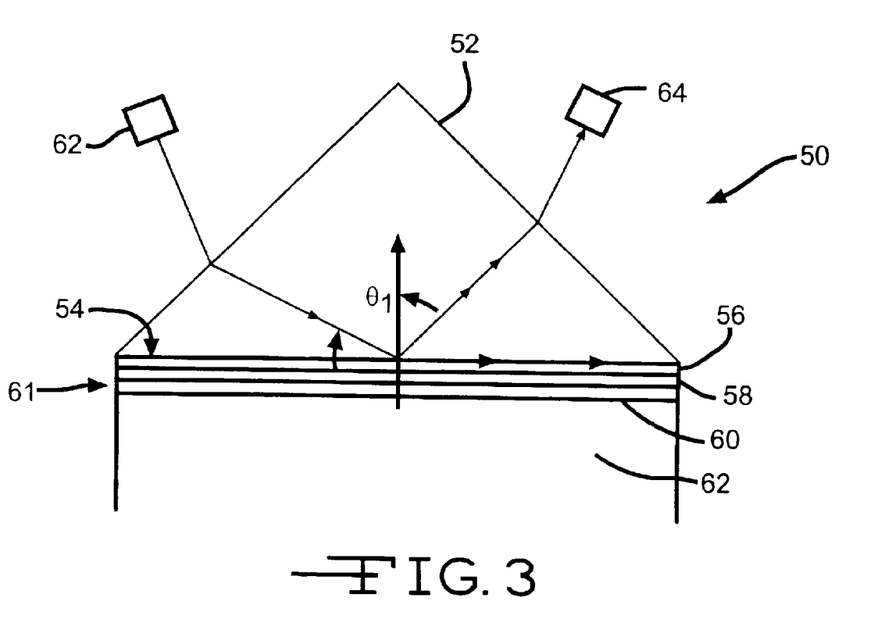
FIG. 3 is a sectional view of a third embodiment of a biosensor that can be used to obtain a waveguide mode resonance with the method of the invention, where the biosensor employs prism coupling.

FIG. 3 is a sectional view that shows the optical layer structure of a sensor 30 to obtain a waveguide mode. Waveguide modes are discussed in "Theory of prism-film couplers and thin film light guides", P. K. Tien and R. Ulrich, Journal of the Optical Society of America, 60, 1325 (1970), which is incorporated herein by reference. The sensor 50 has the same general structure as the prism coupled structure shown in FIG. 1. However the sensor 50 includes a waveguide layer 58 rather than the metal layer 38 of the sensor 30 shown in FIG. 1. The reflected light is coupled out of the wave-guide 58, through the coupling prism 52, and to the detector 64. The structure 61 of the layered materials otherwise operates in the same manner as the structure 41 shown in FIG. 1. The structure comprises a first dielectric medium 56 and second dielectric medium 60. The index of refraction of the waveguide 58 is larger than those of the adjacent dielectric layers 56 and 60 allowing the light wave to remain within the waveguide 58. Excitation of the waveguide mode also has a resonant property that allows for easier detection of changes in the interaction between the antibodies and antigens. The waveguide 58 is also set-up in such a manner that light only couples to the waveguide mode when the incident light is at a certain angle. The layers 56, 58, 60, form a similar structure 61 as described above and as shown in FIGS. 1 and 2 with respect to the double grating structure 10 and the first prism coupled structure 30. The waveguide structure 50 also performs the function of combining the antibodies and antigens in a similar manner as described above. A source of radiation 62 and an optical detector 64 complete the assembly. The source of radiation 62 preferably emits a well-collimated beam of light. The angle of incidence of the light is rotated to the angle $\theta_1$, the mode angle, at which a sharp attenuation in the strength of the total internally reflected beam is observed. An optical detector 64, which can be any suitable device for measuring light, such as a linear pixel array, generally captures the reflected light beam.

While a surface mode is a wave that achieves its primary amplitude at the surface interface of the layered materials and a waveguide mode achieves its primary amplitude as the wave propagates within the waveguide, either wave has the reflected beam intensity profile property that is the focus of the present invention. The above diffraction grating structure and prism-coupled structures can all be used with the method of the invention, described below, since the profile re-shaping phenomenon is independent of the method of surface wave or waveguide mode excitation. Therefore, while the output results will not be identical when using any of the structures shown in FIGS. 1, 2, or 3, all the sensor structures will depict the same profile re-shaping phenomenon.

Figure 4:
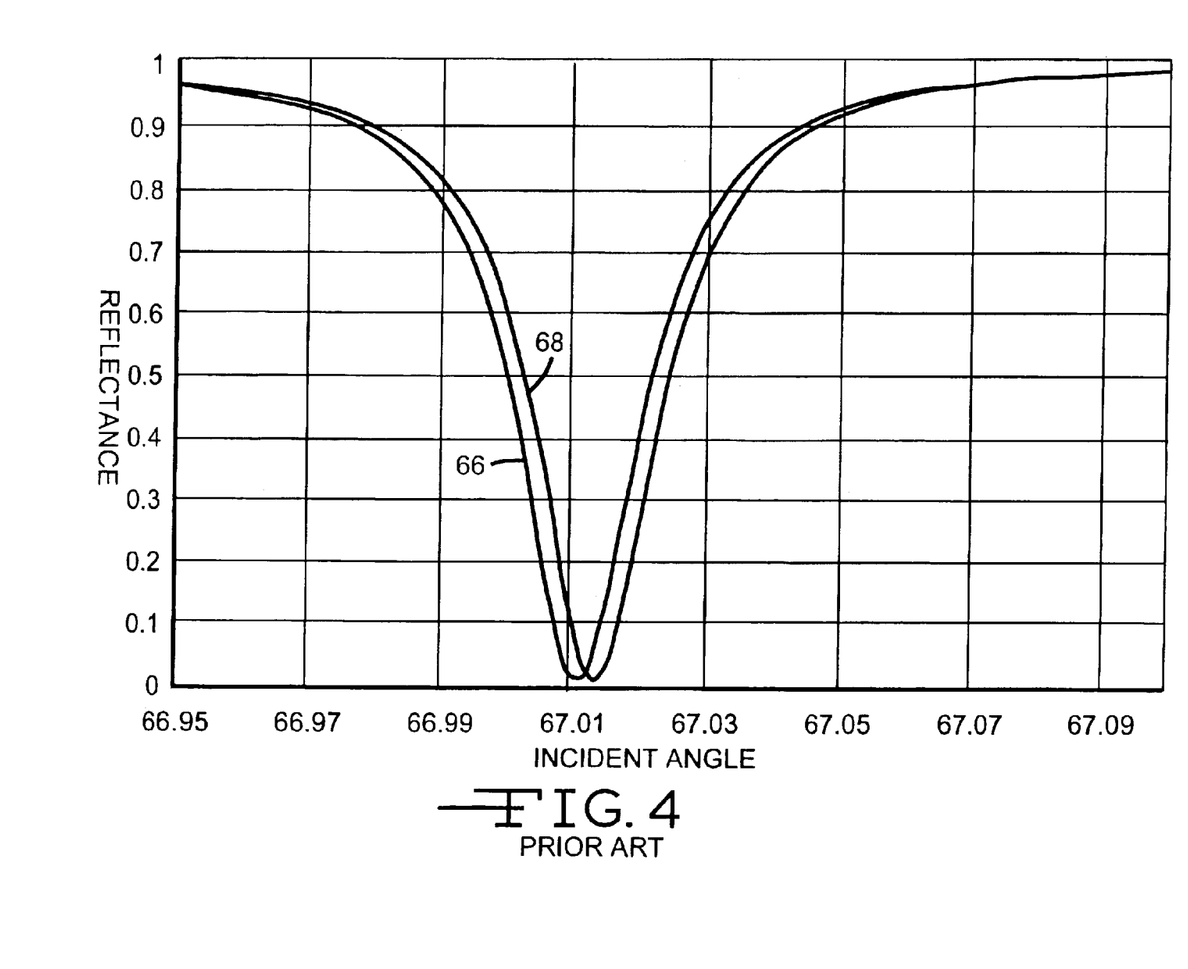
FIG. 4 illustrates the results obtained when measuring the indices of refraction with a biosensor of the type illustrated in FIG. 1 using the prior art method of measuring the total beam intensity wherein the y-axis represents the reflectance and the x-axis represents the incident angle.

FIG. 4 is a plot of the reflectivity or reflectance of a sample versus the angle of incidence of a monochromatic, well-collimated, P-polarized light source over a small angular range, as measured according to the prior art method. FIG. 4 illustrates the results obtained when any of the biosensors illustrated in FIGS. 1, 2, or 3 is used in conjunction with the prior art methods of measuring the total beam intensity to determine the characteristic ATR curve and is included only for reference purposes. This particular example (i.e., FIG. 4) was produced using the prism-coupled LRSP mode biosensor shown in FIG. 1 ATR calculations based on the grating-coupled LRSP geometry defined in FIG. 2 or the prism-coupled wave-guide mode defined in FIG. 3 would each produce ATR curves similar to those shown here in FIG. 4.

The specific numerical values for various parameters associated with the biosensor shown in FIG. 1 are as follows: incident wavelength=0.78 micrometers, prism 32 index of refraction=1.471, first dielectric medium 36 index of refraction=1.35, gold metal layer 38 index of refraction= 0. 1754+i4.9123, first dielectric medium 36 layer thickness= 2.5 micrometers, gold metal layer 38 thickness=0.014 micrometers, and analyte or second dielectric medium 40 index of refraction=1.35. The resulting ATR curve 66 is calculated using the above parameters. The position of the minimum ATR defines the plasmon angle to be 67.012 degrees.

The second curve, curve 68 shows what happens when an antigen layer is brought into contact with the assay solution that contains antibodies. As the antibody is captured out of the solution by the first organic antigen layer the effective index of the second dielectric medium changes slightly. The antigen layer is generally separated from the metal layer by a dielectric buffer layer. Nonetheless, the interaction between the antibodies and antigens changes the refractive index a small amount. Here, it is assumed that the effect of the bonding antigen/antibody reaction results in a changed analyte or second dielectric medium 40 index of refraction equal to 1.35005. From the re-calculated ATR curve 68 the shifted plasmon angle is seen to be 67.014 degrees. It is this shift in the plasmon angle of the two ATR curves 66, 68 by 0.002 degrees in this example, according to the measurement technique of the prior art, which forms the basis of the measurement of the bonding antigen/antibody reaction in all current SPR biosensors. It is understood that the values used above are exemplary only and that the method of the present invention is not limited by the values listed above.

In contrast to the prior art method of measuring changes in optical properties, where the total reflected beam energy is measured at different angles of incidence, the method of the invention involves measuring the intensity profile of the reflected beam at a single incident angle, usually taken to be the plasmon angle or the mode angle. The intensity distribution of the reflected light is measured wthin a transverse beam profile of the total reflected beam. This intensity profile measurement made at a single angle provides the key distinction from the prior art method of measuring the total beam intensity over a range of angles of incidence, the results of which are shown in FIG. 4. The purpose of measuring the beam profile is to detect the pronounced re-shaping of the reflected beam associated with the excitation of the SPR. This resonant reshaping phenomenon was first pointed out by R. Ulrich, "Plane-Wave Analysis of Prism-Film Coupler", Journal of the Optical Society of America, 60, 1337–1350 (1970), which is incorporated herein by reference.

The re-shaping phenomenon is described as follows. When the finite spatial profile of the incident wave is taken into account, by the use of spatial Fourier transform theory, new structure in the profile of the reflected beam is discovered. The amplitude of the reflected field is found to consist of the sum of two terms. The first term is a specular term, which mirrors the profile of the incident wave but is attenuated in amplitude. The second term is a more complicated surface term, which initially builds up its amplitude in the direction of propagation along the interface, but then decays as a damped propagating surface wave downstream. beyond the profile of the specular reflected wave. The total reflected wave is the sum of these two terms and thus can exhibit destructive interference, which significantly alters the reflected profile relative to that of the incident beam. The sensitivity of this profile structure to the index of refraction of the analyte medium forms the basis for the enhanced sensitivity of this new detection scheme relative to the angle-tuned ATR method employed by all prior art SPR biosensors. Therefore, this method stands in sharp contrast to the presently used schemes, which effectively detect the integrated profile resulting from the use of focused light beams.

The method of the invention used to measure the changes in optical properties of layered materials includes directing an incident wave toward the layered materials under conditions that will produce a propagating surface mode in the layered materials. In a preferred embodiment, the incident well-collimated beam is a laser. In a further preferred embodiment, the incident angle of the beam is defined to within the diffraction angle of the laser, which would be on the order of a few milliradians, and as is well known in the art. This is in contrast to the much larger angular spread of a few degrees in most prior art systems that use an LED and a focusing lens. First, an angular scan of the layered system is carried out to generate a measured ATR curve and to locate the plasmon angle, as is well known in the art. Next, with the angle of incidence fixed at or near the plasmon angle, the intensity distribution within the transverse beam profile of the total reflected beam is measured. Then, the index of refraction of the layered materials, usually taken to be the analyte medium, is modified. This can be done in any suitable manner. However, in the preferred embodiment of the invention the index of refraction is modified by reintroducing a liquid serum that contains the test antibody into the structure in such a manner that the liquid contacts the previously layered antigen. The interaction between the antigen layer and the antigens in the solution causes the molecules to bond to the antigen layer, thereby slightly changing the index of refraction of the analyte medium. Without changing the angle of incidence, the intensity distribution within the transverse beam profile of the total reflected beam is then re-measured. It is understood that the angular setting is now slightly off resonance. Finally, the two measured intensity profiles are compared to detect any changes in the index of refraction in the layered materials. The beam profile captured or measured by any of the optical detectors 28, 44, 64 can be converted to usable form by any means, many of which are known in the art.

Figure 5:
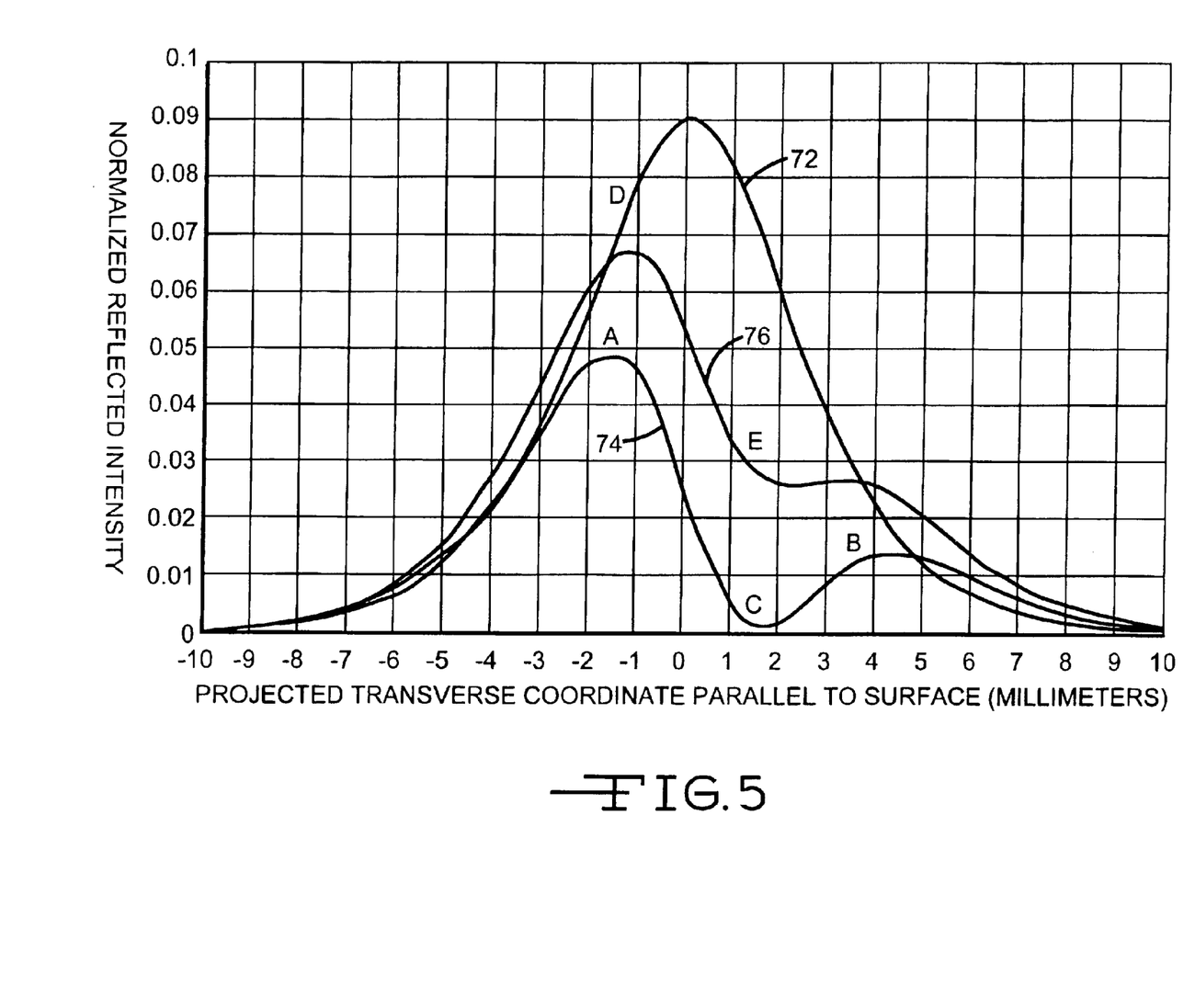
FIG. 5 illustrates the results obtained when determining the indices of refraction with a biosensor of the type illustrated in FIG. 1, using the method of the present invention to measure the beam intensity profile wherein the x-axis represents the transverse beam coordinate projected parallel to the surface and the y-axis represents the normalized reflected intensity.

A comparison of the beam profiles is shown in FIG. 5. This graph plots normalized beam intensity or normalized power per unit area (with 1=100%) versus the transverse beam coordinate projected parallel to the interface in millimeters. The first curve 72 depicts the beam profile of the incident beam in the prism 32 and is shown here for reference purposes only. This curve 72 is the profile of the incident beam reduced by a factor of 0.09 to appear approximately full scale on the reduced ATR scale of FIG. 5. The incident beam shape assumed in these calculations is a hyperbolic secant that approximates the standard symmetric laser profile. Although a full-width at half-maximum (FWHM) of 2.1 mm is used here, a smaller width would be assumed in practice. It should be noted that the FWHM of 5.4 mm displayed in FIG. 5 is projected parallel to the surface such that the measured beam profile is assumed to be calculated as follows: (5.4 mm)(cos 67°)=2.1 mm. All system parameters applied to FIG. 1 and used in the first calculated ATR curve 66 of FIG. 4 are also used here.

The second curve 74 displays the reshaped profile of the reflected beam under the condition that the incident beam is tuned to the resonant angle for excitation of the LRSP mode, which in the Figure is 67.012 degrees. The first specular peak at Point A of curve 74 illustrates that the reflected ATR peak is only about 5% of the incident peak intensity. The second peak at Point B demonstrates that the propagating surface wave reaches a peak intensity of about 1.5% and then decays beyond the envelope of the incident beam. The sharp minimum at Point C results from interference between the specular and surface waves amplitudes.

Finally, the third curve 76 is the reflected profile at the same incident angle but assuming that the effect of the bonding antigen/antibody reaction results in a changed analyte or second dielectric medium 40 index of refraction equal to 1.35005. It is important to note that the incident beam remains fixed at 67.012 degrees and is not tuned to the new surface plasmon angle. At Point D on curve 76 the specular peak has jumped to nearly 7% and more importantly the interference minimum has been replaced by a shoulder structure at Point E of about 2.5%. The percentage values listed in this section are the percent relative to the value of the collimated incident beam measured at its center; and hence the changes in beam intensity profile shown between curves 74 and 76 should be easily detectable. The salient feature of the graph is how much the original profile has been altered by a change in analyte index of only 0.00005. By comparing the reshaped profile curves 74 and 76 in FIG. 5 to the slightly shifted ATR curves 66, 68 in FIG. 4 it is demonstrated that this new profile method exhibits increased sensitivity. When sophisticated software is applied to the reflected profiles displayed in FIG. 5, the sensitivity to an analyte index change will be significantly better than prior art methods. It is understood that the exact values used above are exemplary only and are not meant to limit the values that can be practiced with the present invention. It should be further understood that although the above-described method measures the intensity profile at a specific plasmon angle, the invention can be practiced at any angle in the vicinity of the plasmon angle. In fact if the initial angle used in FIG. 5 was chosen to be 67.014 degrees instead of 67.012 degrees then the two curves 74 and 76 would be effectively interchanged. The relevance of the above is that it is the beam profile measurement that increases the sensitivity of this SPR biosensor, regardless of the specific angle in the vicinity of the plasmon angle that is used.

The theory on re-shaping SPR beam profiles is generally based on planar interfaces. Both the reflected profiles, curves 74 and 76 are calculated using the method of spatial Fourier Transform Theory as may be found in Jon Mathews and R. L. Walker, "Mathematical Methods of Physics", 1970, The Benjamin/Cummings Publishing Company, pp. 101–107. At present there is no equivalent theory for a corrugated surface as found in a diffraction-grating geometry. However, since the characteristic re-shaping of SPR beam profiles is a general property associated with the excitation of a surface wave by a finite-width incident beam and not a property of the method of coupling, either method of coupling (prism-coupling or diffraction-grating) will produce the results described herein. In principle, the beam profile may be observed for both the well-known Kretschmann mode and the more resonant LRSP mode. However, this phenomenon is more easily detectable when the spatial width of the incident beam is on the order of the propagation length of the surface mode or at most up to a factor of five larger than the propagation length. The propagation length of the LRSP mode is introduced in D. Sarid, "Long-Range Surface Plasma Waves on Very Thin Metal Films", Physical Review Letters 47, 1927–1930, (1981) which is incorporated herein by reference. For the Kretschmann mode used with a gold metal layer and a near infrared light source, the design commonly found in most commercially available biosensors, this length scale is less than 50 micrometers. However, a biosensor based on an LRSP mode, with a propagation length an order of magnitude longer may be more practical for observing this effect.

Although the invention herein has been described as using near-infrared light, it is possible to use incident light from elsewhere in the electromagnetic spectrum. In particular, when certain metals, such as silver are used in the layered materials, the use of infrared light can improve the sensitivity of this system. Under these conditions the beam profile reshaping phenomenon may be seen by using the single-boundary Kretschmann mode in the far infrared as reported by W. P. Chen et al., "Excitation of Surface Electromagnetic Waves in Attenuated Total Reflection Prism Configurations", Phys. Rev. Letters 37, 993 (1976), the entire document of which is incorporated herein by reference. Thus it is possible that the use of infrared light will further improve the detectability of bonding antigen/antibody reactions in a single-boundary SPR system.

The principle and mode of operation of this invention have been described in its preferred embodiments. However, it should be noted that this invention can be practiced otherwise than as specifically illustrated and described without departing from its scope.

What is claimed is:

1. A method of measuring changes in optical properties of layered materials comprising:
    directing an incident wave toward the layered materials under conditions that will produce a propagating surface mode in the layered materials, wherein the layered materials have an index of refraction, and wherein the incident wave is directed at a single incident angle with respect to the layered materials;
    measuring an intensity distribution within a transverse beam profile of a total reflected beam;
    modifying the index of refraction of the layered materials;
    re-measuring the intensity distribution within a transverse beam profile of the total reflected beam using an incident wave with the same single incident angle;
    comparing the measured intensity distributions to detect differences in the index of refraction in the layered materials.

2. The method defined in claim 1 further comprising tuning an angle of the incident wave to an optimum angle that maximizes an amplitude of the surface mode.

3. The method defined in claim 1 wherein intensity distribution data corresponding to each of the transverse intensity distributions is analyzed, such that the smallest changes in the transverse beam profile are detected.

4. The method defined in claim 1 wherein the intensity distribution within the transverse beam profile of the total reflected beam is measured as a function of transverse beam position.

5. The method defined in claim 4 wherein the total reflected beam is sensed by an optical detector.

6. The method defined in claim 1 wherein the directed incident wave is a well-collimated beam.

7. The method defined in claim 6 wherein the incident beam has a diameter of not more than 2.1 millimeters at full-width half-maximum.

8. The method defined in claim 7 wherein the beam diameter is between 0.05 millimeters and 1 millimeter at full-width half-maximum.

9. The method defined in claim 5 wherein the transverse beam profile is measured parallel to the surface of the optical detector.

10. The method defined in claim 1 wherein the incident wave comprises electromagnetic radiation whereby the radiation is introduced in such a way that the radiation excites a surface mode at one of a plurality of surfaces comprising the layered materials.

11. The method defined in claim 1 wherein the layered materials comprise a plurality of layers.

12. The method defined in claim 11 wherein a first layer is a dielectric medium.

13. The method defined in claim 12 wherein a second layer is a metal surface.

14. The method defined in claim 13 wherein a third layer is an organic bonding layer between the metal surface and a fourth layer.

15. The method defined in claim 14 wherein the third layer further comprises antigen molecules.

16. The method defined in claim 15 wherein the index of refraction of the layered materials is modified by introducing a fourth layer into contact with the layered materials.

17. The method defined in claim 16 wherein the fourth layer is an organic layer further comprising antibody molecules.

18. A method of measuring changes in optical properties of layered materials comprising:
    directing an incident wave toward the layered materials under conditions that will produce a waveguide mode in the layered materials, wherein the layered materials have an index of refraction, and wherein the incident wave is directed at a single incident angle with respect to the layered materials;
    measuring an intensity distribution within a transverse beam profile of a total reflected beam;
    modifying the index of refraction of the layered materials;
    re-measuring the intensity distribution within a transverse beam profile of the total reflected beam using an incident wave with the same single incident angle;
    comparing the measured intensities to detect differences in the index of refraction in the layered materials.

19. The method defined in claim 18 further comprising tuning an angle of the incident wave to an optimum angle that maximizes an amplitude of the waveguide mode.

20. The method defined in claim 19 wherein the incident wave is directed towards the layered materials at the optimum angle.

21. The method defined in claim 20 wherein the intensity distribution within the transverse beam profile of the total reflected beam is measured as a function of transverse beam position.

22. The method defined in claim 21 wherein the total reflected beam is sensed by an optical detector.

23. The method defined in claim 22 wherein the transverse beam profile is measured parallel to the surface of the optical detector.

24. The method defined in claim 18 wherein the directed incident wave is a well-collimated beam.

25. The method defined in claim 24 wherein the incident well-collimated beam has a diameter of not more than 2.1 millimeters at full-width half-maximum.

26. The method defined in claim 25 wherein the beam diameter is between 0.05 millimeters and 1 millimeter at full-width half-maximum.

27. The method defined in claim 18 wherein the layered materials comprise a plurality of layers.

28. The method defined in claim 27 wherein a first layer is a wave-guide region.

29. The method defined in claim 28 wherein the second layer is an organic bonding layer between the wave-guide region and the third layer.

30. The method defined in claim 29 wherein the third layer is an organic layer further comprising antigen molecules.

31. The method defined in claim 30 wherein the index of refraction of the layered materials is modified by introducing a fourth layer into contact with the layered materials.

32. The method defined in claim 31 wherein the fourth layer is an organic layer further comprising antibody molecules.

33. The method defined in claim 32 wherein the waveguide region of the layered materials is capable of supporting the waveguide mode.

* * * * *